United States Patent
Beaty

[11] Patent Number: 5,816,811
[45] Date of Patent: Oct. 6, 1998

[54] SURGICALLY IMPLANTABLE PROSTHETIC DEVICES

[75] Inventor: Keith D. Beaty, West Palm Beach, Fla.

[73] Assignee: Implant Innovations, Inc., Palm Beach Gardens, Fla.

[21] Appl. No.: 711,398

[22] Filed: Sep. 6, 1996

Related U.S. Application Data

[62] Division of Ser. No. 149,905, Nov. 10, 1993, Pat. No. 5,607,480.

[51] Int. Cl.⁶ ....................................................... A61C 8/00
[52] U.S. Cl. ................................................................ 433/173
[58] Field of Search .................................... 433/173, 174, 433/201.1; 623/16, 18

[56] References Cited

U.S. PATENT DOCUMENTS

| | | | |
|---|---|---|---|
| 3,790,507 | 2/1974 | Hodosh | 433/173 |
| 3,855,638 | 12/1974 | Pilliar | 433/173 |
| 4,180,910 | 1/1980 | Straumann | 433/173 |
| 4,530,116 | 7/1985 | Frey | 623/23 |
| 4,818,559 | 4/1989 | Masaaki et al. | 433/173 |
| 4,865,603 | 9/1989 | Noiles | 623/18 |
| 4,878,914 | 11/1989 | Miwa et al. | 623/16 |
| 5,188,800 | 2/1993 | Green et al. | 422/23 |
| 5,222,983 | 6/1993 | Schmitz et al. | 623/16 |
| 5,258,030 | 11/1993 | Wolfarth et al. | 623/16 |
| 5,316,476 | 5/1994 | Krauser | 433/173 |
| 5,366,374 | 11/1994 | Vlassis | 433/165 |

FOREIGN PATENT DOCUMENTS

| | | |
|---|---|---|
| 0213836 | 11/1987 | European Pat. Off. . |
| 0409810 | 1/1991 | European Pat. Off. . |
| 1148254 | 6/1989 | Japan ........................................ 623/16 |
| 92/05745 | 4/1992 | WIPO . |

OTHER PUBLICATIONS

Wennerberg et al., "Design and Surface Characteristics of 13 Commercially Available Oral Implant Systems," Int. J. Oral Maxillofac Implants, Dec. 27, 1993, vol. 8, pp. 622–633.

ASTM Designation F 86–84, "Standard Practice for Surface Preparation and Marking of Metallic Surgical Implants".

University of Bern (Switzerland), Clinic for Dental Maintenance (Schweizerisch Monatschrift für Zahnheikunde, vol. 86, No. 7, Jul. 1976, pp. 713–727).

Buser, D. et al., "Influence of Surface Characteristics on Bone Integration of Titanium Implants. A Histomorphometric Study In Miniature Pigs", Journal of Biomedical Materials Research, vol. 25, pp. 889–902. (1991).

"Optimization of Surface Micromorphology for Enhanced Osteoblast Responses in Vitro," Bowers et al., Int. J. Oral Maxilofacial Implants, 1992, pp. 302–310.

Gotfredsen, K., et al., "Histomorphometric And Removal Torque Analysis for TiO₂–Blasted Titanium Implants" Clinical Oral Impl. Res., Feb. 6, 1992, pp. 77–84.

Wilke et al., "The Influence of Various Titanium Surfaces on the Interface Shear Strength Between Implants and Bone, Advances in Biomaterials", vol. 9, pp. 309–314.

*Primary Examiner*—John J. Wilson
*Attorney, Agent, or Firm*—Arnold, White & Durkee

[57] ABSTRACT

The surface of a surgically-implantable prosthetic device is impacted with particles of the same material as the device to form the surface into a desired pattern of roughness.

6 Claims, 5 Drawing Sheets

TI/TI6-46B-70PSI-Y

TI/TI6-46B-70PSI-Y

SURGICALLY IMPLANTABLE PROSTHETIC DEVICES

This application is a divisional of application Ser. No. 08/149,905, filed Nov. 10, 1993, entitled Surgically Implantable Prosthetic Devices, now U.S. Pat. No. 5,607,480.

INTRODUCTION

The success of prosthetic devices surgically implanted in living bone depends entirely on achieving an enduring bond between the confronting surfaces of the device and the host bone. A surgical procedure for preparing living bone to receive a surgically implanted prosthetic device has been known for twenty years or more, but considerable controversy remains concerning the ideal properties of the surface of the implanted device which confronts the host bone. This invention relates to processes for improving those surfaces of the prosthetic devices and to devices having the improved surfaces, so as to enhance the quality and durability of bonding between the prosthetic devices and the host bone.

BACKGROUND

It is known through clinical experience extending over several decades that titanium and its dilute alloys have requisite biocompatibility with living bone to be acceptable materials for use in making surgically implantable prosthetic devices when the site of installation is properly prepared to receive them. There is, however, less certainty about the ideal physical properties of the surfaces of the prosthetic devices which confront the host bone.

Accordingly, at the present time, owing to its predictable success, the endosseous dental implant fixture made of titanium is the artificial root most frequently chosen for restoring dentition to edentulous patients. However, that success depends in part on the micromorphologic nature of the surface of the implant fixture which comes in contact with the host bone. The response of cells and tissues at implant interfaces can be affected by surface topography or geometry on a macroscopic basis as well as by surface morphology or roughness on a microscopic basis.

Because there is no standard for surface micromorphology of dental implants, the surfaces of commercial implants have a wide range of available textures. Up to now, it is known that osseointegration of dental implants is dependent, in part, on the attachment and spreading of osteoblast-like cells on the implant surface, and it appears that such cells will attach more readily to rough surfaces than to smooth surfaces, but an optimum surface has yet to be defined. Buser, D. et al "Influence of surface characteristics on bone integration of titanium implants. A histomorphometric study in miniature pigs" Journal of Biomedical Materials Research, Vol. 25, 889–902(1992).

It has been suggested by some that the ideal surface will have pits that have very small dimensions in the nanometer range, and by others that bone growth into a porous surface coat of Ti6AIV4 alloy with pore size between 50 and 150 micrometers is an efficient and rapid means of bonding endosseous dental implants in humans. Buser et al (Ibid) clearly showed that the extent of bone/implant interface is positively correlated with increasing roughness of the implant surface.

Mention of implant topography, or texture, occurs frequently in the literature and patents relating to this subject; for example, U.S. Pat. No. 4,180,910 issued to F. Straumann et al, Jan. 1, 1980, at column 2, lines 59 to 67 describes a dental implant member made of titanium provided with a coating of titanium granules applied to it by flame spraying, producing a rough surface "comprising pores, most of which have a diameter of 1 to 10 $\mu$m, although still smaller pores are also present". Similar results are reported in a published article emanating from the University of Bern (Switzerland), Clinic for Dental Maintenance (Schweizerische Monatschrift fur Zahnheilkunde, Vol. 86, No. 7, July 1976, pp. 713–727). U.S. Pat. No. 3,855,638 issued to Robert M. Pilliar Dec. 24, 1974 discloses a surgical prosthetic device made of a body of a selected material and having on its surface a layer of particles of the same material forming a porous coat of the particles. It has been suggested, e.g: PCT application No. SE91/00672, International Publication No. W092/05745 and date Apr. 16, 1992, to blast the surface of implants of titanium or an alloy of titanium with particles of a titanium oxide.

Prior-known processes for achieving biocompatible surfaces on surgically implantable prosthetic devices have taken many forms, classifiable primarily as:

1. processes which add something to the surface; and
2. processes which take something away from the surface.

Among the first class are coating, cladding and plating processes, which include, as examples, the processes described in the above-mentioned patents to Straumann et al, and to Pilliar, and processes which coat a body with bone-compatible apatite materials, such as hydroxyapatite or whitlockite. The latter has spawned a vast literature which includes U.S. Pat. No. 4,818,559 issued to Hama et al. Apr. 4, 1989. Among the second class are acid etching, ion etching, chemical milling, laser etching and spark erosion. Sometimes processes of both classes are combined, as in the Hama et. al. patent.

It is well understood that the chemical properties of the surfaces of surgically implantable prosthetic devices should as much as possible exclude impurities which could lessen the biocompatibility of the devices. See, Ibid, Pilliar and PCT publication No. W092/05745. Thus, for example, traces of elements of the tools used to turn titanium in a lathe may become embedded in the surface of a device, contaminating the device notwithstanding that the starting piece of titanium may have been "pure" to the governing specification of biocompatibility.

It has been suggested that the type of roughness produced on a chemically pure titanium surface does affect initial biological responses such as cellular attachment and spreading. An irregular rough surface produced by sand blasting appears to be more conducive to cellular attachment than other rough surfaces produced by polishing/grinding or acid etching. (Int. J Oral Maxillofacial Implants 1992;7: 302–310) P. Ducheyne et al, "The Effect of Hydroxyapatite Impregnation on Skeletal Bonding of Porous Coated Implants" J. Biomed. Mater. Res. 14,225–237 (1980) describe a cylindrical plug of stainless steel coated with a porous metal fiber of the same material, with the individual fibers lined with hydroxyapatite, for increasing the rate of bone in growth when implanted in the femur of living dogs.

S. D. Cook et al, "Torsional Stability of HA Coated and Grit-Blasted Titanium Dental Implants" J. Oral Implantol. 18(4)pp 354–65 (1992), in a comparative study in dogs, showed superior interface torsional strength for the HA-coated implants, with interface failure seen to occur primarily at the HA/implant interface.

The present invention is not based essentially on addition to or taking away from the surface of the prosthetic device. While it may fit incidentally into the second class, and in some embodiments it may appropriate properties of the first class, it is primarily concerned with reforming the surface without necessarily removing any material from it or adding any material to it. The invention accordingly addresses new and greatly improved processes for achieving a biocompatible surface on surgically-implantable devices wherein the existing surface is selectively and controllably manipulated to form a new prescribed surface topography or texture.

GENERAL NATURE OF THE INVENTION

It is a general object of the present invention to produce an improved surgically implantable prosthetic device having on its surface a prescribed micromorphology; another object is to produce such a device having on its surface a controllably-prescribed distribution of indentations in the form of pits, dents, scratches and/or craters with dimensions in a controllably-prescribed range.

It is an additional object of the invention to produce an improved surgically implantable device of the type described without contaminating the surface of the device.

A further object of the invention is to teach a process or processes for making the improved device.

According to the invention in one of its more general aspects the surface of a surgically implantable prosthetic device is impacted with particles of a material which is related to the material of the device and preferably harder, e.g: an alloy of that material, in order to form the desired micromorphology without risk of contaminating that surface. For example, a titanium body is impacted with a titanium grit which is not required to remain on the surface. The relative hardness, the quantities, sizes and shapes, of the grit particles, and the impact-velocity of the particles and the direction of their impact, are each selected and controlled with a view to the size, shape, character and distribution of the surface depressions or indentations intended to be formed. Thus, the invention envisions controllably forming surface depressions that are round or elongated (e.g: oval) in shape, that have smooth or sharp-edges contours, that are simple dents or scratches in the surface, or that are craterlike with a berm surrounding or partly surrounding the depression. The particles in the grit preferably have greater hardness than the body of the device. For example, if the device is made of pure titanium the grit particles may be of a dilute alloy that is harder. The grit may be carried in a fluid in which the concentration of the particles may be controlled and the particles may be directed in a stream to achieve a desired distribution and array-pattern of indentations or depressions on the surface of the device.

The grit may include particles of a bone-compatible apatite material, such as hydroxyapatite or whitlockite, some of which are deliberately embedded in the surface of the titanium body by the process of the invention. In a particular embodiment of the invention, the grit may be predominantly or even entirely composed of the apatite material. Such embodiments, unlike prior devices coated with the known coatings, resist separation of the apatite material from the titanium body when the prosthetic device is put into use.

Processes for making the invention include steps for forming, selectively, each form of depression in the surface of the device, under controllable conditions. Such steps include, as one example, preparing a fluidized bed of grit particles in which the hardness, shapes, sizes, compositions and concentrations of the particles can be precisely controlled and directing a stream of the fluid bearing the particles under controlled velocity and direction toward the surface of the device. In another embodiment the process includes the steps of providing the grit particles in a whirling cyclonic fluid and locating the device in the whirling fluid while slowly turning it to expose its surface to impact by the particles. The carrier fluid may be a gas or a liquid. The particles may be propelled without a carrier. Heat is not necessary to the process.

The invention has the ability to provide surface treatments for surgically implantable prosthetic devices which can be tailored to the advances in clinical knowledge which are occurring and will continue to occur in the future. It has the further ability to provide a prescribed surface micromorphology for clinical research and investigation designed to elucidate paths leading to such advances; thus, the invention has as a further and very important object the advancement of progress in the design of surgically implantable prosthetic devices.

That titanium particles may have surface layers of naturally-forming oxides of titanium, to a thickness of perhaps 80 Angstrom units, is not material to the invention. The invention does not require the presence of any oxide(s), and is fully functional without them.

Implant devices with surfaces selectively prepared according to the present invention may be subjected to an additional process according to U.S. Pat. No. 5,188,800, owned by the Assignee if the present application, so as to increase wettability of the surface. That additional process involves placing the implant in a plasma cleaning device, therein subjecting the implant to a flow of substantially pure gas (e.g: an inert gas selected from Krypton, Argon, and mixtures thereof; or oxygen), continually removing gas from the plasma cleaning device so as to maintain a vacuum therein in the range about 20 to about 5,000 microns, and continuing the flow and the vacuum for a period of time to clean and sterilize the implant and until the surface develops a surface contact angle of about 20 degrees or less, preferably about 10 degrees or less, and more preferably about 5 degrees or less. The disclosure of said U.S. Pat. No. 5,188,800 is incorporated herein by reference.

DESCRIPTION OF EXEMPLARY EMBODIMENTS OF THE INVENTION

The invention will be more fully explained in the following description of exemplary embodiments with the aid of the accompanying drawings, in which:

FIG. 1 schematically illustrates a surface modified to have a depression surrounded by a berm;

FIG. 2 shows a means to modify a surface with a projectile aimed to impact the surface normally;

FIG. 3 schematically illustrates a surface modified to have a depression without a berm;

Figure 6:
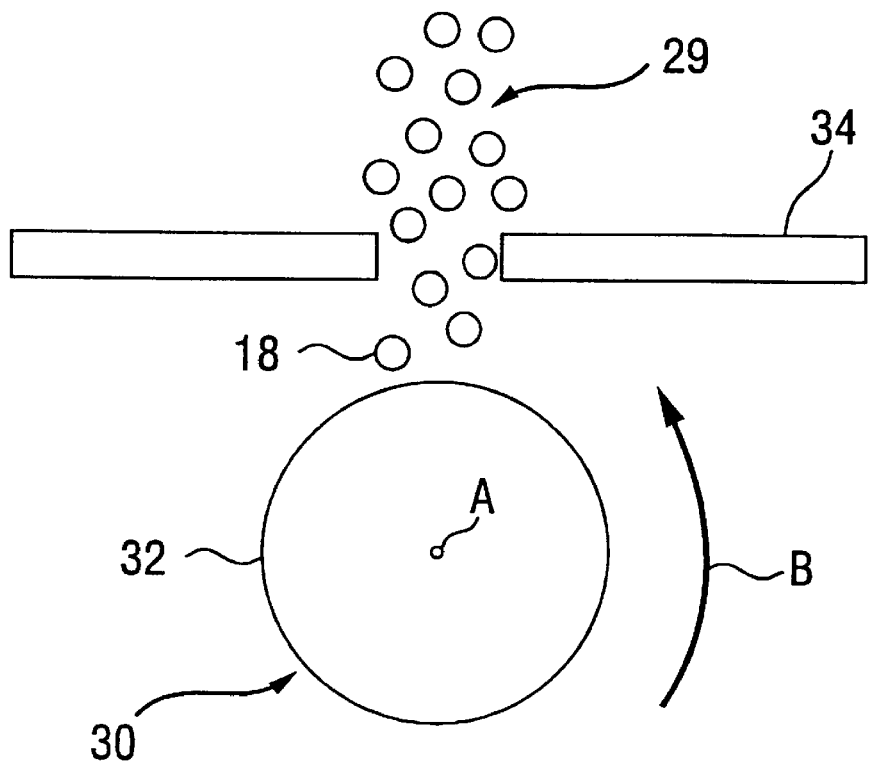
FIG. 6 shows a scheme for impacting a surface with a stream of projectiles aimed to impact the surface substantially normally.
Figure 6A:
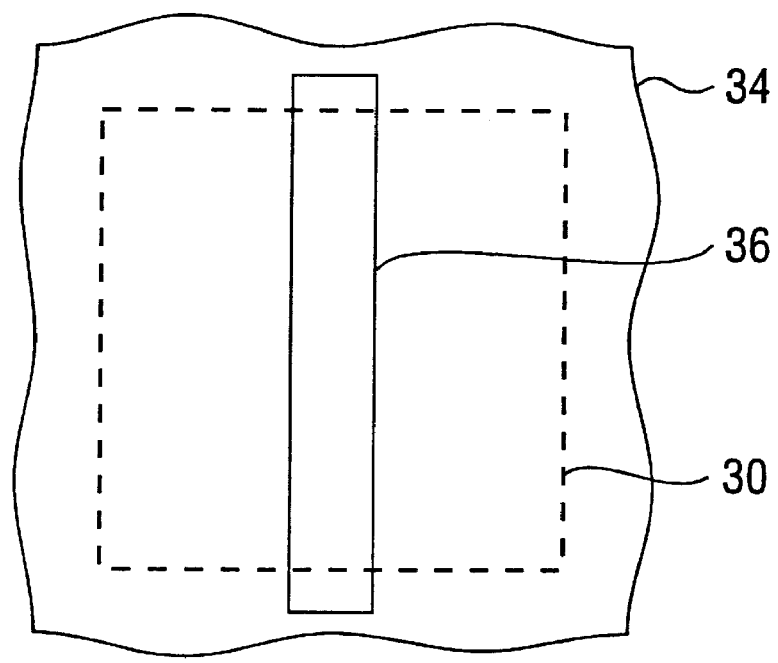
Figure 7:
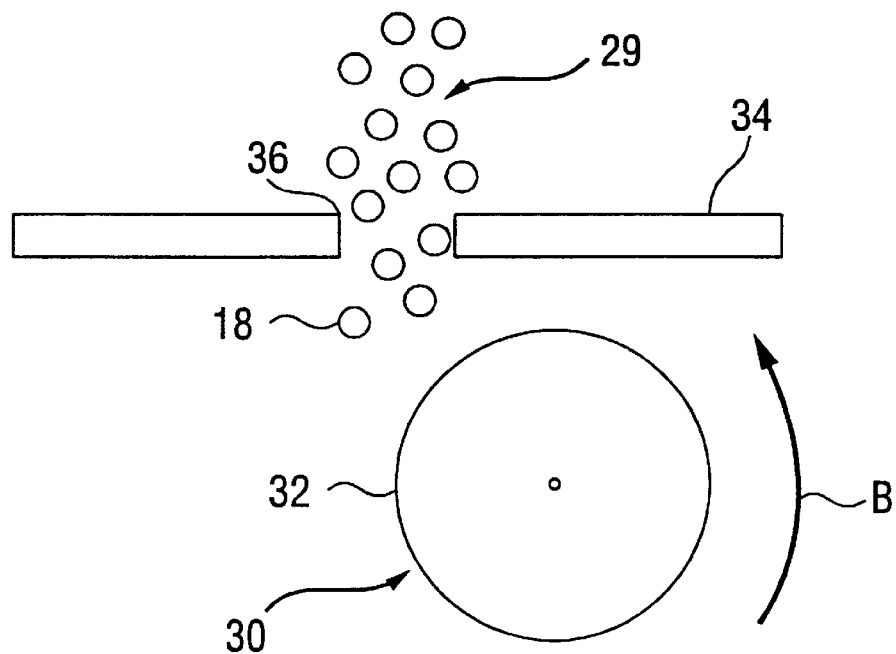
Figure 8:
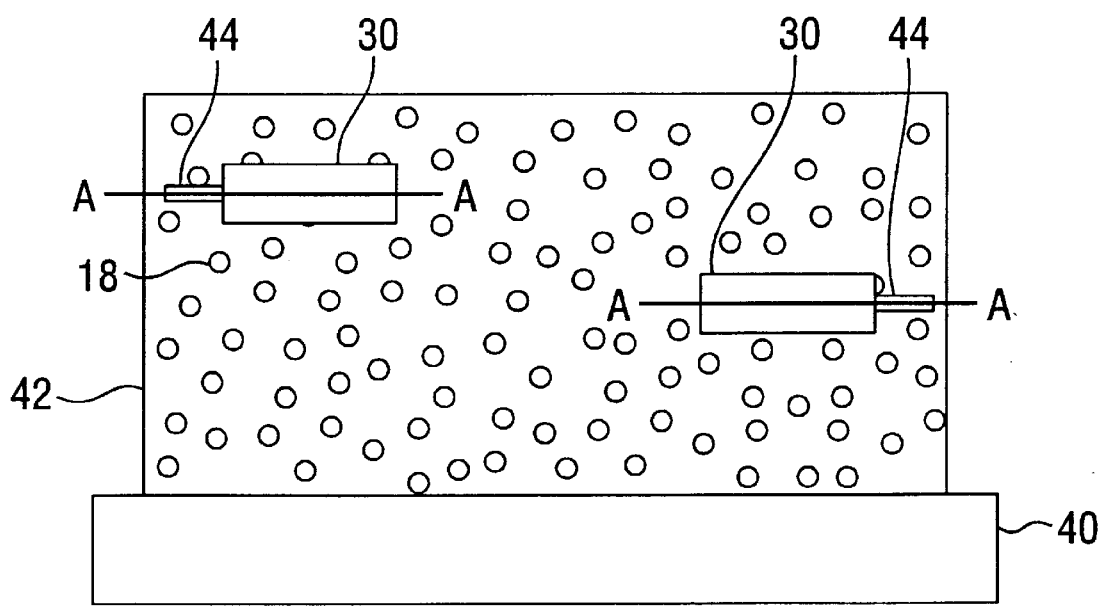
Figure 9A:
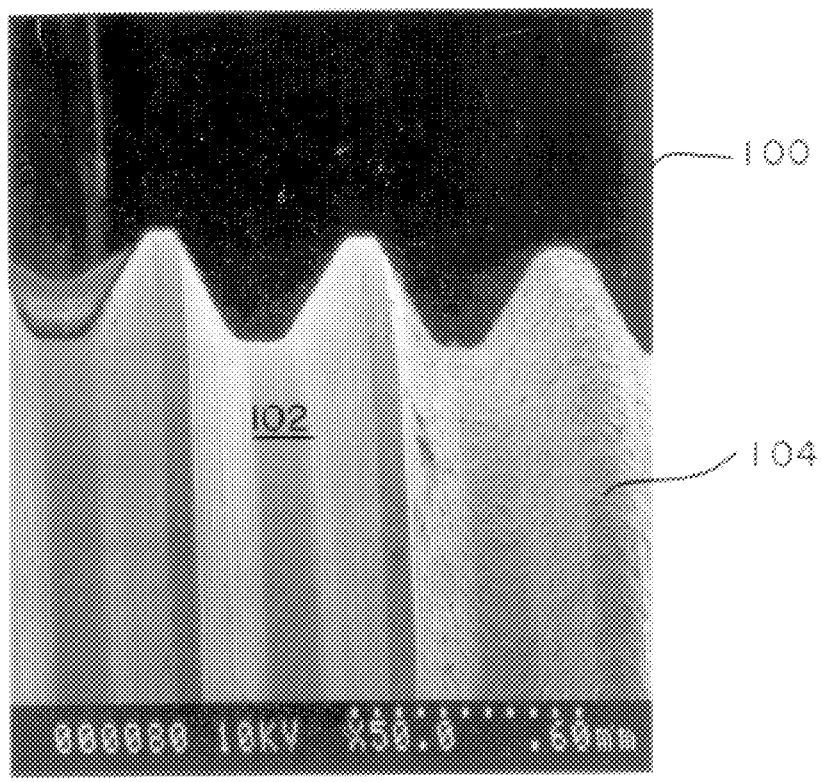
Figure 9B:
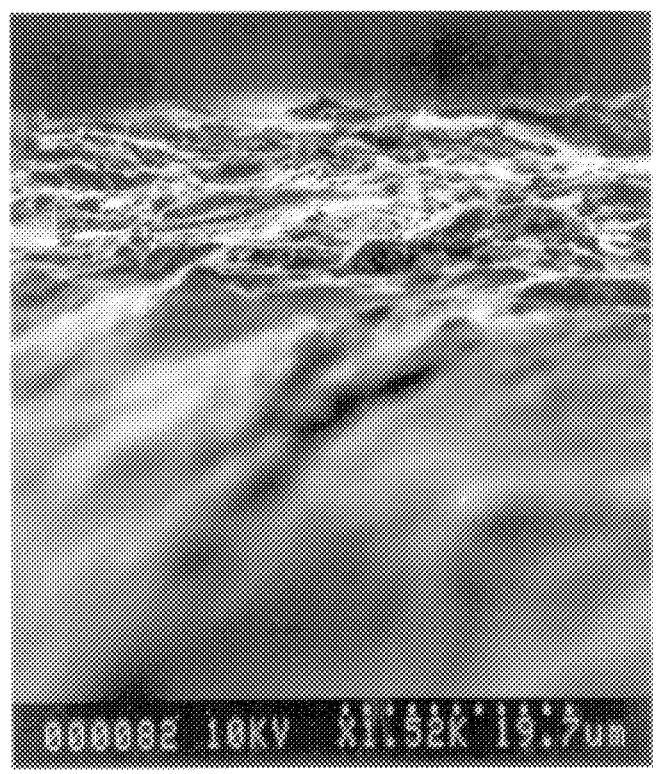

FIG. 6A schematically shows a partial plan view of FIG. 6;

FIG. 7 shows a scheme for impacting a surface with a stream of projectiles aimed to impact the surface obliquely;

FIG. 8 shows a scheme for impacting a surface in a cloud of projectiles generated in a fluidized bed; and FIGS. 9A and 9B are xerocopies of two photographs showing a dental implant surface—modified according to the invention.

Figure 1:
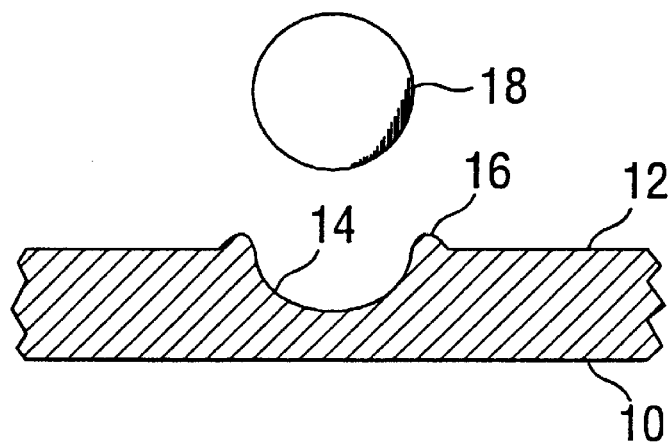
Figure 2:
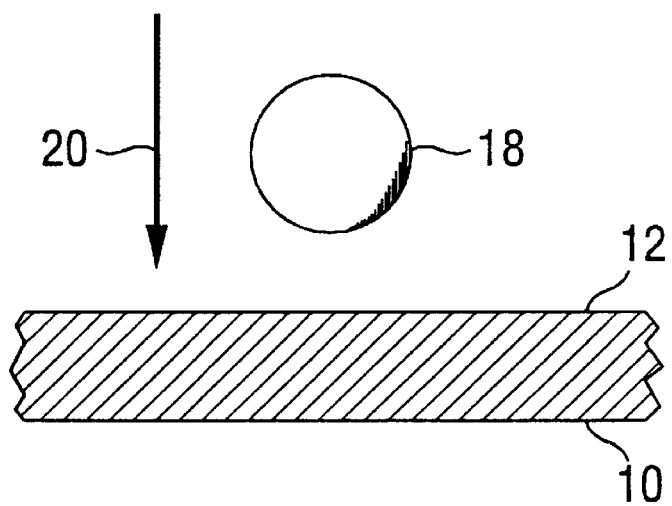
Figure 3:
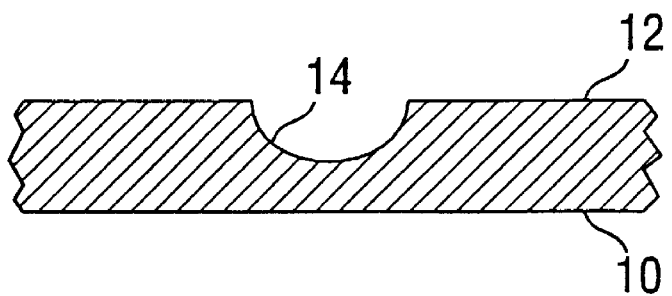

In FIGS. 1 and 2 a segment of an article 10, which article may be a dental implant fixture, has an outer surface 12 which has been modified (FIG. 1) to have a depression 14 surrounded by a berm 16. The depression has substantially round perimeter and the berm is substantially symmetrical around that perimeter. This depression may be formed by impacting the surface 12 with a projectile 18 aimed to hit the surface normally, as is represented by the arrow 20 in FIG. 2. Depending on the velocity of the projectile on impact the depression may have the berm 12, or it may be without a berm as is illustrated in FIG. 3. The mass of the projectile, its hardness, its velocity on impact, its surface characteristics and its shape will all combine to determine the characteristics of the depression, such as it shape and depth.

Figure 4A:
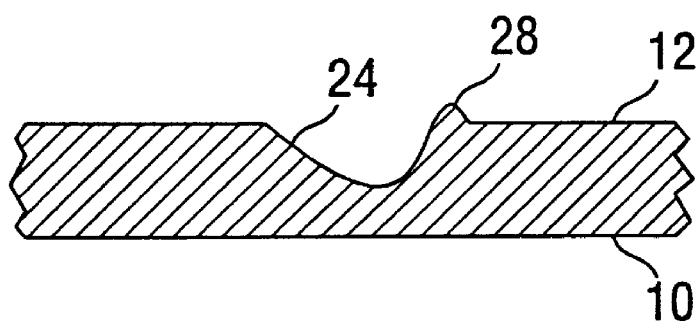
FIG. 4A is a section on line X—X of FIG. 4B.
Figure 4B:
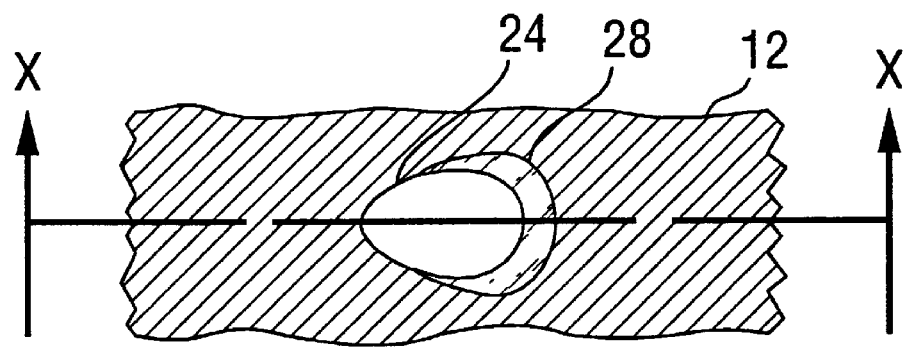
FIG. 4B is a top view schematically illustrating a surface modified to have a non-symmetrical depression partly surrounded by a non-symmetrical berm.
Figure 5:
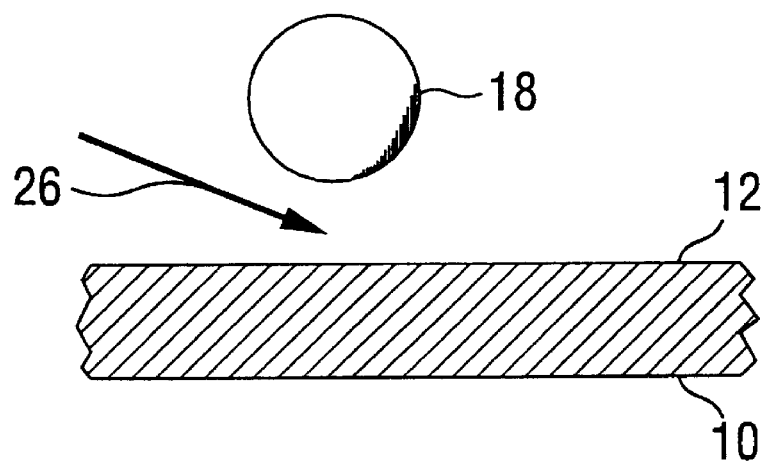
FIG. 5 shows a means to modify a surface with a projectile aimed to impact the surface obliquely.

FIGS. 4 and 5 shows a non-symmetrical depression 24 (FIG. 4) in the surface 12, formed by impacting the surface with the projectile 18 aimed to impact the surface at an oblique angle as is represented by the arrow 26 in FIG. 5. The depression may have a non-symmetrical berm 28, or not, depending on the above-mentioned properties of the projectile.

A stream 29 of projectiles 18 may be aimed to impact the surface 32 of a cylindrical body 30 substantially normally using the scheme shown in FIG. 6. A mask 34 fitted with a slot 36 is placed adjacent the surface 32 in the path of the stream of projectiles, so that those projectiles which pass through the slot will impact the surface 32 substantially normally. The slot 36 has a length at least as great as the axial length of the body 30, as is represented in FIG. 6A, so that projectiles 18 may impact the surface 32 along its entire length. The body 30 may be rotated on its axis A, counter-clockwise as represented by the curved arrow B, or vice versa, to expose the entire surface 32 to projectiles 18. The number of depressions formed on the surface 32 will depend primarily on the density of projectiles in the stream and the speed of rotation of the body.

The stream of projectiles may be aimed obliquely, or tangentially, at the surface 32 using the scheme shown in FIG. 7. The character of the pits formed in this manner will depend, additionally, on the direction of rotation of the body 30.

In FIG. 8 a fluidized bed 40 provides a cloud of particles 18 in the confined space 42 above the bed. Several articles (e.g: dental implants) 30 are in that space, each mounted to a support 44 for rotation around its longitudinal axis A—A. The density of this cloud and the velocity of individual particles in it are established as desired to effect the required modification of the surfaces of the articles 30. By this means a uniform pattern of depressions may be produced on the surface of each article.

In another scheme, the implant is located in a whirling cyclonic stream of particles 18 (not shown), where it may be rotated to expose its entire surface to oncoming particles. In this scheme, as in the others described and illustrated herein, prolonged exposure of the implant surface will result in an overlapping mass of irregularities to the point of destroying features of individual impressions, dents, scratches and the like.

To add a bone-growth promoting agent to a surface that has been modified according to the invention one may substitute particles of that agent for some or all of the surface-modifying projectiles 18 in any of the above-described processes and apparatus. Thus, for example, one may add particles of hydroxy-apatite, whitlockite or another agent, such as a carrier for a medicament (e.g: a bone morphogenic protein),to the particles 18 of titanium or its alloy, or substitute same after the implant surface has been modified, and continue the process to place particles of the bone-growth promoting agent in the depressions formed on that surface. If the implant surface has non-symmetrical depressions 24 or the like, as illustrated in FIGS. 4A and 4B, for example, the bone-growth promoting agent can be projected into those depressions while the implant 30 is being rotated counter-clockwise, for example, as seen in FIG. 7. If, further, the implant is designed to be screwed into the patient's bone socket with a counter-clockwise rotation, small chips of bone will be gathered into the depressions, and be packed therein on top of the growth-promoting agent. The invention envisions such an embodiment of the invention, which will inherently resist separation of the growth-promoting agent from the implant surface 12, thereby overcoming a problem which is indigenous to the prior art.

The shape of the particles 18 etc may be controlled with the aid of fluidized bed apparatus of the kind illustrated in FIG. 8. If initially particles in the cloud are rough-shaped with sharp edges, corners and the like, one may maintain the cloud for an extended time interval during which the particles in the cloud will impact each other smoothing away the sharp corners and edges. Particles which are substantially round may be produced in this way, in order to form substantially round depressions on the surfaces of the articles 30. If the article 30 is made of c.p.titanium and it is desired to use projectiles which are harder than the article 30, the projectiles may be made of the alloy TiAl6V4.

The apparatus and processes illustrated in the drawings are exemplary. Other methods and means to impact particles on a surface, which may be used in practicing the present invention, are mentioned in the above-references PCT Application, for example.

An example of a dental implant surface modified according to the invention is shown in FIGS. 9A and 9B. FIG. 9A is a 50x photographic enlargement of a portion of a screw-type dental implant only part of the surface of which has been modified. The unmodified part 102 is the threaded surface produced by machine turning of a billet of titanium. The modified part 104 was impacted with a Ti6AlV4 grit (−325 mesh) sprayed at 90 degrees substantially normal to the surface at pressure =70 PSI (indicated on the photograph) for approximately 3–5 minutes while the implant was rotated at an angular speed of about 10 seconds per revolution. The array of dots at the lower right of FIG. 9A measures 0.60 mm in the axial direction of the implant. FIG. 9B is a further enlarged view looking along the modified surface 104. As is apparent in these figures the implant procedure was continued long enough to substantially obliterate features of individual depressions, dents, scratches and the like, so as to produce an intense, substantially uniform roughness of the bone-contacting surface of the implant. It has been observed that individual depressions and dents, will have transverse dimensions (e.g: diameters) about half the size of the impacting grit particles. Thus, a grit of −325 mesh, having particles in the size range from about 10–15 microns, will generally produce depressions about 5–10 microns across at the surface of the implant.

I claim:

1. A substantially cylindrical dental implant having on its surface a plurality of discrete depressions, each of said depressions having a shape corresponding to a projectile impacting said surface coincident to rotation of said implant in a selected direction about a longitudinal axis of said implant, said depressions facing forward relative to said selected direction of rotation and having a longer dimension generally parallel to said selected direction of rotation, said implant being adapted for installation in a receiving bore in a patient's jawbone by turning said implant in said bore in said selected direction of rotation, at least some of said depressions receiving chips of said bone in response to rotation of said implant in said bore.

2. An implant according to claim 1 including bone-growth-enhancing material in at least some of said depressions, positioned to be retained in said depressions by said chips when the latter are received therein.

3. An implant according to claim 2 in which said bone-growth-enhancing material is selected from the group consisting of hydroxyapatite materials, whitlockite materials, and medicaments including without limitation bone morphogenic protein.

4. An implant according to claim 1 in which at least some of said depressions have berms partially surrounding the rearward boundaries of said depressions.

5. An implant according to claim 1 in which said depressions have smaller dimensions ranging in size from about 5 microns to about 10 microns.

6. An implant according to claim 1 wherein said depressions have a surface contact angle of about 20 degrees or less.

* * * * *